United States Patent [19]

Kater

[11] 4,094,822

[45] June 13, 1978

[54] BIO-EVENT ELECTRODE MATERIAL

[76] Inventor: John A. R. Kater, 583 Traverse Dr., Costa Mesa, Calif. 92626

[21] Appl. No.: 734,405

[22] Filed: Oct. 21, 1976

Related U.S. Application Data

[63] Continuation-in-part of Ser. No. 566,335, Dec. 26, 1974, Pat. No. 3,993,049.

[51] Int. Cl.$^2$ .............................................. H01B 1/02
[52] U.S. Cl. ................................... 252/512; 252/518; 128/2.06 E; 128/2.1 E
[58] Field of Search ............................ 252/512, 518; 128/2.06 E, 2.1 E, DIG. 4, 417 A

[56] References Cited

U.S. PATENT DOCUMENTS

| | | | |
|---|---|---|---|
| 3,834,373 | 9/1974 | Sato | 128/2.06 E |
| 3,946,730 | 3/1976 | Monter | 128/2.06 E |
| 3,998,215 | 12/1976 | Anderson et al. | 128/2.06 E |
| 4,002,221 | 1/1977 | Buchalter | 252/518 X |

*Primary Examiner*—Benjamin R. Padgett
*Assistant Examiner*—E. Suzanne Parr
*Attorney, Agent, or Firm*—Grover A. Frater

[57] ABSTRACT

An electrolyte for a bio-electric event measuring electrode combines a salt with adhesive. The adhesive serves as the vehicle for dispersing solvent to form the electrolyte in a solid or semisolid mixture. The adhesive serves further as a structural element in holding the parts of a practical electrode together and in making the electrode adhere to a subject's skin.

4 Claims, No Drawings

BIO-EVENT ELECTRODE MATERIAL

RELATIONSHIP TO OTHER APPLICATIONS

This application is a continuation-in-part of application for U.S. Pat., Ser. No. 536,335, filed by me on Dec. 26, 1974, now U.S. Pat. No. 3,993,049, and entitled IMPROVED ELECTRODES AND MATERIAL THEREFOR.

This invention relates to improvements in compositions for incorporation in electrodes to be used in measuring bio-electric events.

The magnitude of the electric potentials that characterize such events are very small. Contact potentials which result from ionic activity at liquid-to-liquid and liquid-to-metal and metal-to-metal interfaces may have the same order of magnitude as bio-electric potentials. Moreover, junction potentials are not uniform. They vary with micro changes in ion concentration that results from other than the event of interest. Such variations in junction potentials are called "artifacts," and if they are occasioned by relative motion between the elements that constitute a measuring circuit as an incident to motion of the subject, or otherwise, they are called "motion artifacts."

It is possible to minimize junction potentials and motion artifacts, and to arrange circuits in which junction potentials are closely predictable, by proper selection of the circuit materials and the attaching elements. In particular, the materials at interfaces between dissimilar materials are selected so that ion exchange proceeds reversably. Junctions of that kind are called non-polarizing junctions, and the materials which provide best results are well known.

However, the problem of providing a suitable electrode for application to skin cannot be optimized by electro-chemical considerations alone. The cardiac patient whose heart action must be monitored and who must wear electrodes for protracted periods, astronauts who must wear electrodes for many days, are all concerned with the irritation which those electrodes produce. More than discomfort is involved. The skin may be damaged and discolored.

It is possible to optimize the electro-chemical action and construction of an electrode while minimizing the possibility of electrical motion artifacts. That can be accomplished to some degree by an electrode which includes a sponge soaked with electrolyte. The sponge is carried in a cup and has a silver coated stud overlying the sponge. That arrangement is used in a commercially available electrode. It requires a relatively heavy salt concentration in the electrolyte to reduce the resistivity of the junction to an acceptable value and it requires a large area of adhesive to retain the cup and sponge in contact with the skin. That construction may solve much of the motion artifact problem, but the necessarily heavy salt concentration results in undue irritation. It is one of the objects of this invention to provide an electrolyte material which will provide the best available electro-chemical behavior and which has mechanical properties that enable it to perform some of the functions that were previously performed by structural elements of prior electrodes to the end that a much wider range of structural form becomes practical.

Another object of the invention is to provide an electrolyte material which has a long shelf life and which is easily and inexpensively manufactured. The days are gone, or should be, when the electro-cardiagraph encephlograph technicians smeared jel on the patient's body and strapped down, or taped down, a metal button or plate. Modern procedures and cleanliness standards, and the need for optimum performance equipment dictate that electrodes not be reused. A fresh electrode is used in each instance. Thus, electrodes are required to be disposable and that term implies an electrode that is packaged in sterile, ready-to-use condition. If possible, the disposable product should be inexpensive. That requires an electrolyte material which is inexpensive, or which, because of its physical characteristics, permits the use of inexpensive electrode structures.

Some disposable electrodes require the addition of electrolyte in liquid or jel form immediately prior to use. Others may be impregnated with, or carry the electrolyte, in liquid or jel form. But that kind often must be specially handled to prevent squeezing out of the electrolyte material, and in general, has the difficulty that shelf life is relatively short. An object of the invention is to provide an electrode, the electrolyte in which is a solid or semi-solid, which does not require special handling, which can be adequately protected by a minimum package, and which has a very long shelf life. These, and other objects and advantages of the invention are realized by the provision of a combination adhesive and electrolyte mixture performing the entire ionic transfer and adhesive function. The combined adhesive and electrolyte substance is formed by mixing a salt in an adhesive which includes, or has added to it, a solvent for the salt. In the preferred form, the adhesive in the mixture is water soluble. The primary solvent should have a low vapor pressure so that it does not evaporate away completely. If the adhesive is also water soluble, perspiration will not interfere with attachment of the electrode to the skin, and cleaning after removal of the electrode is simplified. The salt should include a metal salt and the adhesive-electrolyte, in preferred form, includes current collectors made of the same metal that is includes in the salt. One advantage of the invention is that not all of the salt need be metal salt, and, to some extent, salt content can be reduced by the addition of current collecting metal. All that is required is to provide a reversible ion transfer path and that is done by including metal, salt of what should ordinarily be the same metal, and a solvent for the salt. The primary solvent should be one that will not evaporate completely so that the electrolyte is instantly operable. However, in many applications, instant operation is not required. The electrolyte will still be operative in a very short time if it becomes completely dry. It is customary to clean the skin area to which an electrolyte is applied, and that cleaning can be done with water or an aquaeous alcohol solution. If the electrolyte is applied to a skin area that has been so cleaned, the small amount of moisture that remains is entirely adequate to activate a previously dry electrolyte. Even if no water is added, perspiration issuing from under the electrolyte will render it operative in a matter of seconds.

While the adhesive-electrolyte of the invention has other uses, its primary use is in measuring bio-electric events, and in that application the material bridges the space between some metal conductor and a test point which is usually the skin of a subject. That function can be accomplished by physically bridging the space from the subject to the conductor with ions and a medium in which those ions are mobile. That is accomplished by bridging the space with a salt in which a salt is dissolved. To avoid development of various potentials across the salt, the salt is, in whole or in part, salt of the same metal that forms the surface of the conductor. The resistivity of the path and its stability is enhanced by keeping the path short and by providing parallel paths. That can be accomplished by the inclusion of powders, or bits otherwise formed, of the same metal in the electrolyte.

The fact that the salt must be in solution presents three mechanical problems. First, it is necessary to retain the solvent so that it can be brought into contact with a subject at the desired place. Second, it must be held in contact with that place for a protracted period. Third, it must not evaporate away. In the prior art, those problems were handled mechanically. In one prior art electrode, the electrolyte is contained in a sponge which is held in a cup. The cup is taped, open side down, to the surface of the pateint's skin. A large area tape is employed to hold the cup in place. To prevent evaporation, the electrodes are contained in hermetically sealed packages until they are used. The invention solves the mechanical problems by including a solvent which is made a part of an adhesive material. The solvent is combined with the salt simply by mixing the salt in the adhesive. Resulting mixture serves both as the electrolyte and as the means for making the electrolyte adhere to the subject and to the metal connector. In the case of prior art electrolytes, it has always been necessary to package them in such a way that will prevent evaporation. That is not true in the case of the invention. While hermetic sealing is not harmful, and is useful in those instances in which the electrolyte is to be immediately useful, it is not necessary in the preferred form of the invention.

There are good solvents which cause little skin irritation, which have very low vapor pressure, and which are solvents, both for the electrolyte salt and for suitable adhesives. In fact, in some cases, the solvent is the adhesive. The invention employs such solvents. In the preferred embodiment, it employs solvents of that kind which are themselves soluble in water so that no problems will be created by perspiration or other application of water. To facilitate discussion, the term "adhesive-electrolyte" means a mixture of adhesive and salt. The mixture will also contain a solvent as a component of the adhesive, or as an added component, but the term denotes the mixture even if the solvent has evaporated.

In addition to serving as an adhesive, the adhesive component in the adhesive-electrolyte material serves substantially the same function as does the jel in prior art electrodes. Thus, it serves as a filler in which the concentration of salt can be varied and by which the salt is dispersed more or leas uniformly. It serves as the vehicle for containing or retaining the solvent so that it, too, will be dispersed relatively uniformly throughout the body of electrolyte.

The adhesive is a non-conductor of electricity, but the dissolved metal salts are ions and they and the metal powder are conductive. The resistivity exhibited by the electrode measured from its lower face to the connector varies with the proportion of salt and powdered metal to adhesive. The proportions are not critical, so long as ionic conductivity is maintained. Total resistance is lowered by increasing the area of contact between skin and the adhesive-electrolyte material. The increased area made possible by the invention permits a reduction in salt concentration and a consequent reduction in irritation.

The metal in the salt, in the metal powders that are dispersed in the adhesive-electrolyte, may be any of the materials that are customarily used in reference electrodes and in bio-electrodes. Silver is a good choice, and in that case, the salt would be an alloy of the silver. The standard salt is AgCl. Use of the adhesive-electrolyte at the invention makes it unnecessary to use adhesive tapes and the like. As a consequence, the test area engaged by an adhesive-electrolyte of the invention can have a larger area. As a consequence, the number of parallel flow paths is increased and resistance is lowered. Some of the materials that are ordinarily not selected for use in electrolyte jels because of high resistivity are excellent choices for use in the invention. That is particularly true of a combination zinc and zinc-carbonate, and zinc and zinc-citrate. The salts, zinc-carbonate and zinc-citrate, are less an irritant when applied to human and animal skin than are the conventional salts. One of the advantages of the invention is that it can use the zinc zinc-carbonate and the zinc zinc-citrate combination.

Many adhesives are suitable, and their selection is well within the skill of adhesive technologists. To preserve a semi-solid character, a humectant, or vapor pressure suppressant, is included. In the case of some adhesives, it is advantageous to include a small quantity of mold inhibitor, but that, too, is part of standard adhesive technology. By way of example, some suitable adhesive bases are poly-acrylamide, poly-vinyl-pyrolidone, poly-vinyl alcohol, poly-vinyl-pyridines, and cellulose derivatives.

In addition to the qualities set out above, adhesives may be formulated to have varying degrees of wet tack, adhesive strength, water resistance, remoistenability, and viscosity. Poly-vinyl alcohol adhesives are now preferred. A good remoistenable adhesive for surface electrode has the following formula:

15–25% poly-vinyl alcohol, degree of polymerization (D.P.) = 1700 / 88% hydrolysed;
5–7.5% boric acid;
1.5–2.5% carboxy methyl cellulose;
5–10% glycerol;
Balance — water.

Borax, or boric acid, is used to increase the viscosity whereby "wet tack" is increased. Other thickening agents such as carboxy methyl cellulose may be used either as a substitute for borax or boric acid, or for addition to those substances. Viscosity can also be increased by using fillers such as clay and fumed silica. To maintain wet tack during storage, a plasticizer such as polyethylene glycol or glycerol may be used.

If a more moisture resistant adhesive is desired, the formula may be adjusted so that it has the following proportions of ingredients:

8–15% poly-vinyl alcohol, D.P. = 1750; 98% hydrolysed;
5–7% boric acid;
1.5–2.5% carboxy methyl cellulose;
5–10% glycerol;
Balance — water.

In either of these, bacterial growth may be prevented by adding 0.5% sodium benzoate.

I claim:

1. An electrolyte material for use in producing electrodes comprising a mixture of adhesive, a metal salt, powdered metal of the same kind as the metal of the salt and a solvent in which both said adhesive and said salt are soluble.

2. The invention defined in claim 1 in which the metal in the powdered metal and in the salt is zinc.

3. The invention defined in claim 1 in which said metal is zinc and said salt is zinc citrate.

4. An electrolyte material for use in producing electrodes comprising a mixture of adhesive, a metal salt and a solvent in which both said adhesive and said salt are soluble:

the adhesive including from 15–25% poly-vinyl alcohol, 5–7.5% boric acid, 1.5–2.5% carboxy methyl cellulose, 5–10% glycerol, and balance water.

\* \* \* \* \*